United States Patent [19]

Masini

[11] Patent Number: 5,716,361
[45] Date of Patent: Feb. 10, 1998

[54] BONE CUTTING GUIDES FOR USE IN THE IMPLANTATION OF PROSTHETIC JOINT COMPONENTS

[76] Inventor: Michael A. Masini, 4817 Hillway Ct., Ann Arbor, Mich. 48105

[21] Appl. No.: 556,812

[22] Filed: Nov. 2, 1995

[51] Int. Cl.⁶ .................................................. A61B 17/615
[52] U.S. Cl. .............................. 606/86; 606/88; 606/82
[58] Field of Search ........................ 606/88, 87, 96, 606/82, 76, 86; 623/20

[56] References Cited

U.S. PATENT DOCUMENTS

| | | | |
|---|---|---|---|
| 3,868,730 | 3/1975 | Kaufer et al. | 3/1 |
| 4,936,847 | 6/1990 | Manginelli | 623/23 |
| 4,938,769 | 7/1990 | Shaw | 623/20 |
| 4,944,757 | 7/1990 | Martinez et al. | 623/20 |
| 4,944,760 | 7/1990 | Kenna | 623/20 |
| 5,092,869 | 3/1992 | Waldron | 606/82 |
| 5,122,144 | 6/1992 | Bert et al. | 606/88 |
| 5,129,909 | 7/1992 | Sutherland | 606/88 |
| 5,234,433 | 8/1993 | Bert et al. | 606/88 |
| 5,236,432 | 8/1993 | Masten, III et al. | 606/88 |
| 5,250,050 | 10/1993 | Poggie et al. | 606/79 |
| 5,258,032 | 11/1993 | Bertin | 606/88 |
| 5,342,367 | 8/1994 | Ferrante et al. | 606/86 |
| 5,364,401 | 11/1994 | Ferrante et al. | 606/84 |
| 5,364,402 | 11/1994 | Mumme et al. | 606/88 |
| 5,458,645 | 10/1995 | Bertin | 623/20 |
| 5,569,259 | 10/1996 | Ferrante et al. | 606/87 |

*Primary Examiner*—Michael Buiz
*Assistant Examiner*—Daphna Shai
*Attorney, Agent, or Firm*—Gifford, Krass, Groh, Sprinkle, Patmore, Anderson & Citkowski

[57] ABSTRACT

Improved bone cutting guides enable a surgeon to better gauge required resection characteristics. In one embodiment at least a portion of the guide is transparent, thereby enabling the user to optimize cut estimates and to visualize the resection as it is being performed. In another embodiment, at least a portion of the outer surface of the body is shaped to interact with another bone or prosthetic element associated with a joint, thereby enabling the device to function both as a trial and as a cutting guide. In this embodiment as well the guide may be at least partially transparent to improve visualization. Although primarily intended for use in femorat-side knee arthroplasty, the invention is applicable to any procedure which might benefit from improved bone-cutting accuracy.

8 Claims, 5 Drawing Sheets

5,716,361

BONE CUTTING GUIDES FOR USE IN THE IMPLANTATION OF PROSTHETIC JOINT COMPONENTS

FIELD OF THE INVENTION

This invention concerns arthroplasty, and, more particularly, resides in improved cutting guides having features to better assist a surgeon in preparing a bone, for example, to receive an implant.

BACKGROUND OF THE INVENTION

Whether for primary or revision arthroplasty, cutting guides are typically employed to ensure that the bone saw performs resections corresponding to mating surfaces of the prosthetic component. For example, in a femoral knee replacement, cutting guides or blocks are temporarily secured to the distal end of the femoral shaft, and include slots into which the blade of an oscillating saw is inserted to shape the end of the bone in accordance with corresponding surfaces of the prosthetic element.

In the case of a revision, the procedure is usually more elaborate due to deterioration of the previously prepared surfaces resulting from decomposition of the bone/prosthesis interface, necrosis, and other factors. Cutting blocks are also typically used in revision procedures, though bone deficiency often renders stabilization of the block impossible. In addition, if the cutting block includes a stem, the positioning of the stemmed implant can alter the fit of the final prothesis relative to the bone. More recently introduced techniques attempt to base the cuts on an intramedullary guide to which additional cutting blocks are mounted. Though such approaches improve bone cutting accuracy; there remains an unacceptable margin of error, the correction of which in some cases requiring a freehand shaping of the bone.

SUMMARY OF THE INVENTION

The present invention accordingly provides improved cutting guides which enable one performing a resection to better predict and execute required cue characteristics. Broadly, at least a portion of the body comprising the cutting guide is transparent, thereby enabling the practitioner to better estimate cut depth and/or visualize the resection as it is being performed. Preferably one or more slots are used to guide a cutting saw, with the volume of the body surrounding the slots being transparent.

In one embodiment, at least a portion of the outer surface of the body is further shaped to interact with another bone or prosthetic element as part of a joint, thereby enabling the device to function both as a trial and as a cutting guide. For example, if adapted for use in femoral knee arthroplasty, the outer shape of the body may include condylar protrusions which cooperate with corresponding tibial surfaces or prosthetic inserts. In this combination trial/cutting-guide embodiment the device may likewise advantageously be at least partially transparent to assist in estimating cut orientation or depth, and to visualize a particular resection in progress. Although primarily intended for use in conjunction with preparing a bone surface to receive a prosthetic component, the invention is applicable to any bone-cutting procedure which might benefit from improved accuracy.

DETAILED DESCRIPTION OF THE PREFERRED EMBODIMENTS

Figure 1:
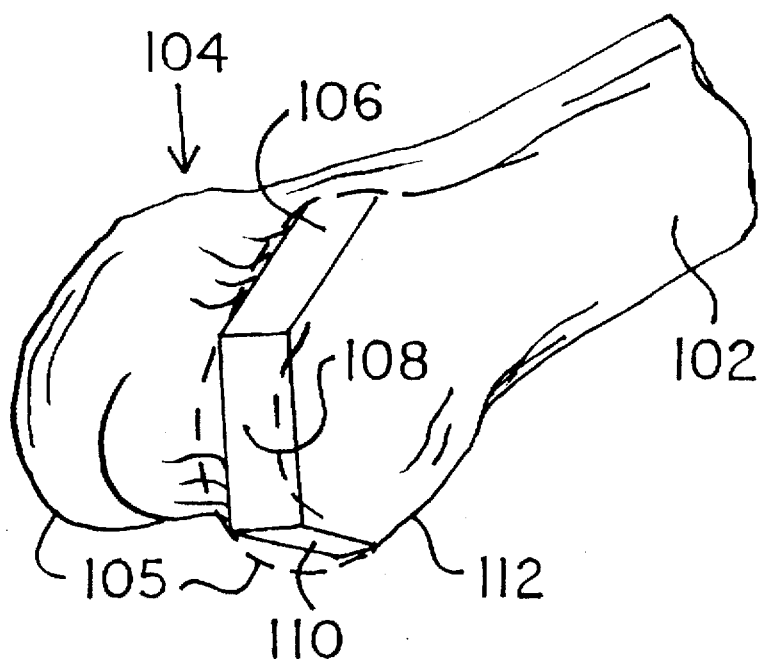
FIG. 1 is an oblique drawing of the distal end of a femur, showing some of the resections typically used in conjunction with prosthetic implantation.

In FIG. 1 there is depicted a distal end portion 104 of a femur 102, which terminates in two bulbous protrusions 105 termed the medial and lateral condyles, which mate and engage with corresponding surfaces in the proximal end of the tibia. As a result of disease or injury, these mating surfaces, ordinarily smooth and cushioned by an intervening cartilage layer, disintegrate and/or become misshapen, resulting in restricted movement and pain.

To ameliorate these conditions, the orthopedic surgeon removes the unhealthy bone stock and replaces it with one or more metallic components which adhere to appropriately prepared bone surfaces and approximate the outer, cortical layer of a healthy bone. To prepare the existing damaged or diseased bone to accept the implant components, various resections are made in a predetermined manner in correspondence with the inner surfaces of the implant. Using the femoral example of FIG. 1, a saw guide is used to form resected surfaces resulting from an anterior chamfer cut 106, distal femoral articular surface cut 108, posterior chamfer cut 110, posterior-articular surface cut 104 112, and/or anterior articular surface cut, which is typically performed prior to the articular chamfer cut. Although these cuts represent resections made in conjunction with a standard implant technique, more, fewer or different surfaces may be required, depending upon the level of deterioration or other circumstances.

Depending upon the saw guide used, either the cuts associated with only one of the condyles may be resected, or, alternatively, a guide having a dual set of slots may be utilized to trim both condyles simultaneously. A singular type fixture is shown, for example, in U.S. Pat. No. 5,122,144, whereas guides having double sets of slots are shown in U.S. Pat. Nos. 5,129,909 and 5,364,401. Numerous other examples are evident in the prior art, some of which are in commercial usage. The cuts associated with revision arthroplasty of the femoral component in a knee replacement are similar to those depicted in FIG. 1, though now additional bone stock must be removed, and additional cuts closer to the central axis of the bone are typically made to accommodate a one-piece replacement unit having a intercondylar strengthening structure and posts extending therefrom for intramedullary implantation. Such a revision knee prosthesis is shown, for example, in U.S. Pat. No. 4,936,847.

Whether for primary or revision arthroplasty, the saw guides involved are without exception now constructed of metal, and they are therefore visually opaque. This results in a substantial piece of hardware which may be washed, sterilized and used repeatedly in numerous procedures, but, being opaque, the orthopedic surgeon is simply unable to see what he or she is doing while making the various bony cuts. As a result, it is often standard practice to make one or more cuts with the guide in place, then move the guide aside in order to view the interface, to ensure that sufficient bone has been removed to facilitate the most ideal cement interface between the resected bone and implant component. This trial-and-error process not only consumes valuable time during the operation, but may lead to the removal of more bone stock than necessary to achieve fixation.

During revision arthroplasty, such trial-and-error is that much more complicated and arduous, owing to the increased number of resected surfaces involved, and the need to ensure that these surfaces and the medullary stem are all properly aligned during the testing of trial implants and the attachment of the final prosthetic device. In the event of a misalignment, the surgeon may choose to use a final implant having a smaller than optimal diameter stem, for example, to take up the slack upon discovering a slight misalignment with respect to the stem and the resected surfaces. This, in turn, may lead to an undesirable "play" between the stem of the prosthesis and the reamed medullary canal, and/or the need for medullary cementation which might otherwise be unnecessary.

According to this invention, then, improved cutting guides are provided to better assist the surgeon in performing accurate resections in an efficient manner. For example, guides adapted for use with primary arthroplasty have transparent features according to this invention, at least in the vicinity of the saw-receiving slots, thus enabling the surgeon to visualize the way in which the existing bone makes contact with the inner surfaces of the guide, and therefore facilitates a much more exacting initial set of cuts, in most cases, ideally eliminating trial-and-error entirely. In the case of revision work, the cutting guide itself contains condylar and other outer surfaces enabling it to function both as a cutting guide and as a trial. Accordingly, once an initial trial procedure is carried out, the various resections may be performed, with a greater likelihood that they will be properly located, thereby increasing accuracy. Although a revision guide according to this invention need not be transparent, the combination of a combined trial/cutting guide constructed of a transparent material is preferred to realize the advantages set forth above.

Figure 2:
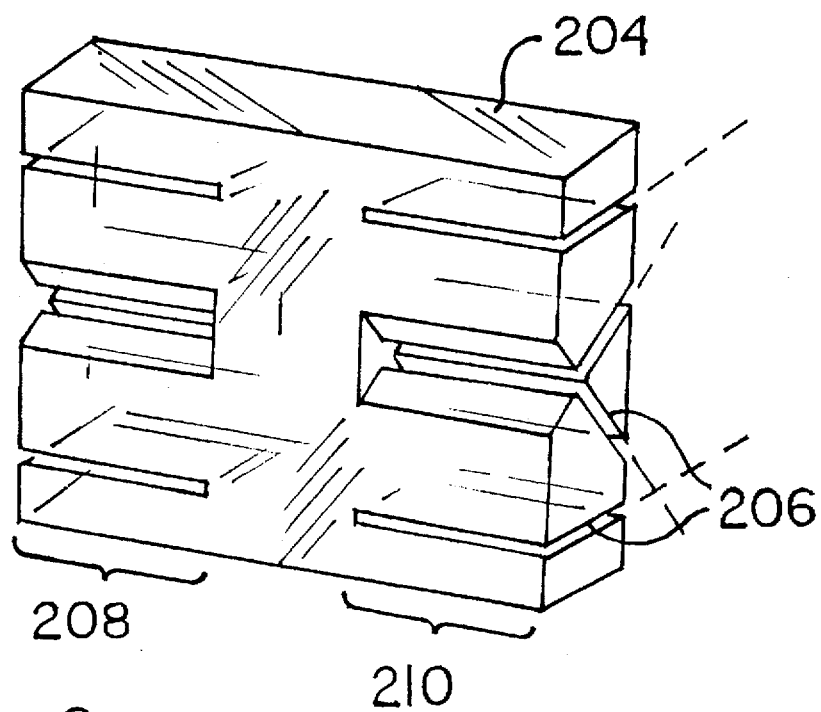
FIG. 2 is an oblique drawing of a cutting guide adapted for primary femoral knee arthroplasty which, according to the invention, is constructed of transparent material.

FIG. 2 illustrates one version of a cutting block constructed in accordance with the invention, in this case a guide for use in making initial articular surface and chamfer cuts. Positioning of the block assumes the surgeon has first made a distal femoral articular surface cut against which the backside (not shown) of block 204 is seated while making these further resections, the chamfer cuts being angular with respect thereto. This block 204 may be held against the bone through any attachment or stabilization means, including screws, pins, braces or other fixtures so long as the guide is appropriately secured. Importantly, and unlike all existing guides of this type, at least the right and left portions 208 and 210 are composed of a transparent material, and, preferably, the entire unit is clear and constructed of acrylic, polycarbonate or any other plastic or material substantial enough to withstand the oscillations of a bone saw or other cutting tool, yet sufficiently transparent to enable a surgeon to visualize the surfaces to be resected in conjunction with a particular procedure. Preferably, this unit and others to be described of a cast plastic material such as acrylic or Lucite, having polished surfaces, where necessary, improve visualization.

In the case of primary arthroplasty, a cutting guide according to the invention need not assume the characteristics of that shown in FIG. 2, but may assume any suitable form and may be used for any bone-forming purpose, whether or not resulting from trauma. For example, the unit may resemble that shown in FIG. 20 of U.S. Pat. No. 5,234,433, which further includes a guide slot to accommodate not only the cuts just described, but, in addition, the distal femoral articular surface cut creating surface 108 in FIG. 1. For that matter, the broad principles of this invention are applicable to any type of cutting fixture, whether slotted or otherwise, adapted for use for prosthetic resection which might benefit from having any transparent portions or panels to assist the surgeon in better visualizing the bone preparation process. This embodiment and those discussed below may also be adapted for use with cutting tools other than saw blades, including osteotomes, router bits, etc.

Reference will now be made to FIGS. 3–8, which represent embodiments of the invention more suitable revision arthroplasty. Before discussing the improved devices and methods made possible through the invention, however, existing approaches will first be discussed with particular regard to femoral knee surgery. In preparing the femur for a revision implant, the procedure may typically first include a drilling and reaming of the medullary canal to accept a sleeve and rod which extends outward and past the distal tip of the femoral shaft, and onto which various components are temporarily secured and stabilized to facilitate the various resections. For example, to perform the distal revision resection, an outrigger may be secured to the protruding stem and onto this placed a revision distal femoral cutting block, typically further secured with pins, screws, or other means engaged with the anterior cortex. Such a distal cutting guide typically includes various slots on either side to accommodate the lateral and medial resections at different depths according to the level of bone loss on either side.

Having prepared the distal surfaces, this first cutting block is removed and an anterior/posterior cutting block is installed onto the stem along with spacers in the event of different depths of the lateral and medial distal resections. With the anterior/posterior cutting block secured in place, again with pins or screws, the anterior and posterolateral lateral cuts are made. Although the anterior cut is typically easily visualized as this region of the femoral shaft is fully exposed during the procedure, as with the lateral resection (s), the posterolateral and posteromedial cuts are almost entirely hidden from view. Once the anterior and posterior resections are carried out, the cutting guide associated therewith is typically removed, and onto the medullary stem there is placed yet another guide used to perform notch and chamfer resections.

Figure 3:
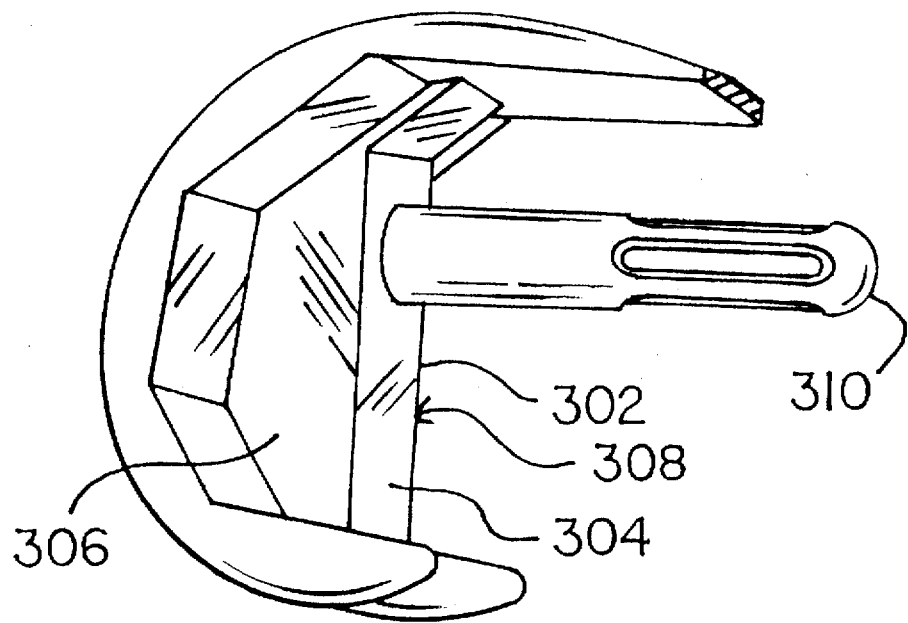
FIG. 3 is an oblique drawing of an existing prosthetic component adapted for mounting on the distal end of the femoral shaft including an intercondylar box structure.

FIG. 3 illustrates a typical prior-art revision implant, and additionally shows the orientation of the notch or "box" cuts to accommodate the intercondylar structure 302, which includes a transverse surface 304 and side surfaces 306 and 308 (not visible). The structure is box-shaped so that flat saw blades may be used to resect the bone and provide a more intimate and stable interface. As discussed above, this boxlike structure 302 provides strengthening between the two condylar halves, and allows room for superior post protrusion in posterior-stabilized designs. The structure 302 also supports the stem 310, which is threadingly or compress-fit thereinto. A notch and chamfer cutting guide is typically used for the chamfer cuts and the cuts associated with the sides 306 and 308 of the intercondylar box, although the stem is typically removed to perform proximal anterior chamfer resections. The stem of the fixture must also be removed in order to make the transverse cut corresponding to the surface 304.

Once all such guides or their equivalents have been used for the various cuts, the orthopedic surgeon typically must further progress through a trial reduction procedure which has matching inner surfaces, but varying thicknesses between the inner surfaces and the outer joint surfaces, which are each tested, in turn, to ensure a correct joint line and femur-to-tibia orientation. Trial polyethylene inserts are also selected to provide maximum range of motion and stability, at which point the femoral component may be implanted, in some cases utilizing spacers to accommodate the depth of cut determined as a function of bone loss. Such spacers typically clip into place, as shown in FIGS. 1 through 4 of U.S. Pat. No. 4,936,847.

It should be evident from the steps just described, that numerous guides must be resorted to as part of a lengthy trial-and-error procedure which, even when carried out in a comprehensive manner, may lead to slight or even gross misalignments upon fixation of the final implant components. The present invention solves many of these problems by providing cutting guides having transparent sections enabling the surgeon to visualize the underlying bone stock before, during and after each resection. In the case of the revision situation, or as part of a primary procedure wherein cutting blocks have been used, the invention further eliminates the need for a protracted trial reduction procedure by providing a cutting guide in the shape of the final implant component, thereby ensuring that once the guide is removed, the final implant component will inherently match the executed resections, thereby saving considerable time while improving accuracy.

Figure 4:
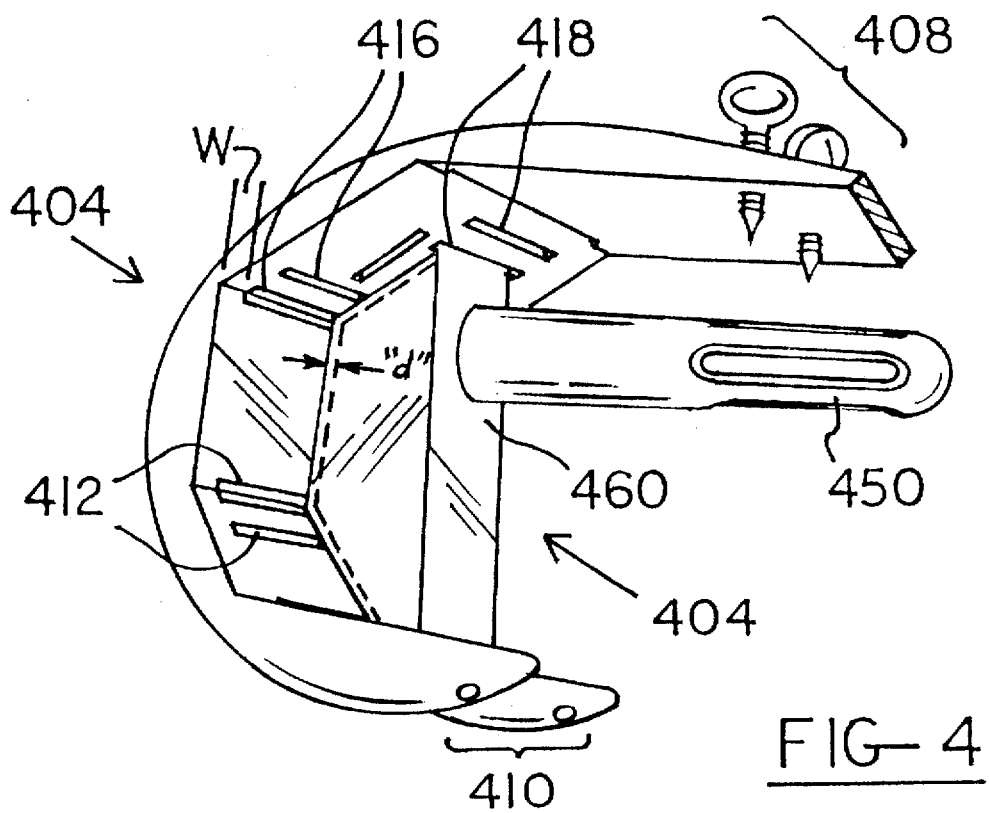
FIG. 4 is an improved cutting guide according to the invention, which includes outer surfaces appropriate to trial testing combined with cutting guides to facilitate efficient resection.

One version of a cutting block according to the invention for femoral knee revision work is depicted in FIG. 4. In this particular embodiment, a combination trial and cutting guide is provided under the assumption that box cuts have previously been made to accept the intercondylar structure 404. Broadly, in this case, the device includes one or more inner surfaces which are configured for correspondence with the resections carried out during the primary procedure, but, according to the invention, the device also includes outer surfaces which approximate the trial prosthesis or final implant shape, including outer condyle surface protrusions, only one side of which is partially visible as 404 in the figure. The device also includes a femoral stem 450, which may be detachable, as well as means for temporarily securing the device to the distal end of the femoral shaft, such as thumb screws 408, which are adapted for engagement with anterior cortical regions, or, as an alternative, stabilization pin holes 410 associated with securing the device laterally or posteriorly. Any type of temporary securement means may be substituted for this optional feature, including tightening bands; outriggers, braces, or any combination of manually operated fasteners or pin-receiving holes or guides, so long as the unit is held in position throughout the procedure.

To simultaneously function as a cutting guide, the device of FIG. 4 also includes one or more slots such as 412 into which a conventional, oscillating saw blade may be inserted to perform a required resection. In the embodiment depicted in FIG. 4, the device is preferably somewhat wider than the final implant, by an amount depicted as "W" shown in the figure, to provide additional material beyond the slotted areas for greater structural stability. Inner surfaces of the device are proportioned, where necessary, by an amount "d" representative of the thickness of the cutting tool used to ensure that, once the combination trial/cutting guide is removed, the final implant mates accurately against the surfaces resected. Preferably the device accommodates sufficient slots and/or surfaces to perform all of the cuts necessary before the installation of a conventional revision prosthetic component, though alternative embodiments may include more or fewer such slots to accommodate a particular or specialized procedure. Depending upon the particular resection to be performed, multiple slots may also be provided to shape a particular surface, the depth of the slot finally relied upon being a function of bone deterioration in a particular region. For example, FIG. 4 shows a set of two slots 416 for the distal condylar cuts and two slots 418 associated with trimming the bottom of the box resections. Preferably, such multiple slots, which may be two or more, are separated by an amount related to existing spacers, for example, 4 mm.

Figure 5:
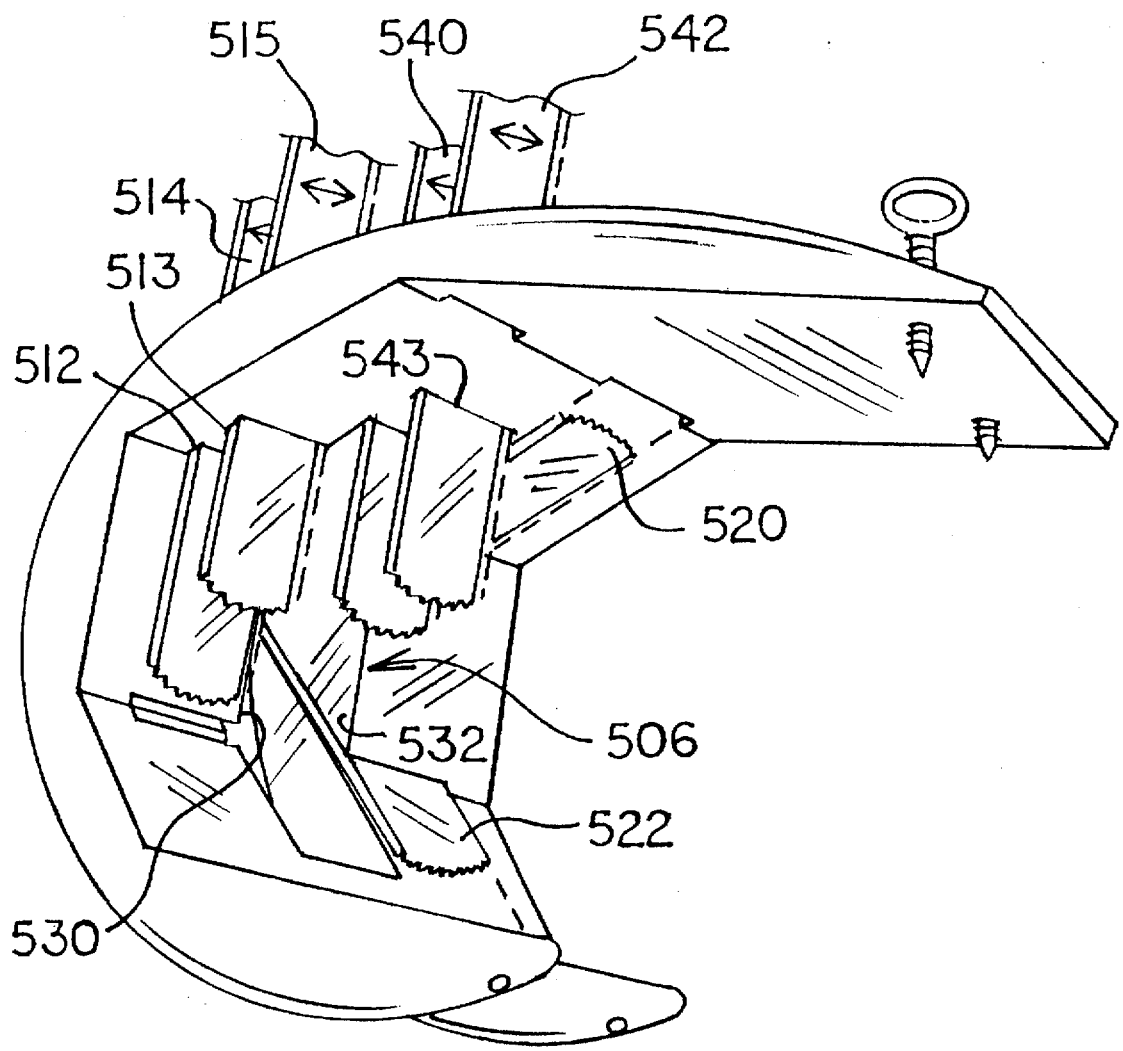
FIG. 5 illustrates from an oblique perspective an alternative embodiment of the invention which facilitates box cuts if not already present.

It should already be apparent that the invention is suitable to femoral knee revision arthroplasty whether or not box cuts have been provided as part of a primary procedure. If provided, the device of FIG. 4 may be used directly; if not, the device of FIGS. 5–8 may alternatively be used. The structure shown in FIG. 5 is quite similar to that depicted in FIG. 4, except the box structure 404 has been replaced with a passageway 506. The device still includes outer condylar surfaces, however, enabling the device to be used as both a trial and a cutting guide. This figure also shows an oscillating saw blade being placed in different slots or against different surfaces to provide the requisite cuts. For example, saw blades 514 and 515 inserted through slots 512 or 513, may be used to form transverse intercondyle cuts, whereas, blades in positions 520 and 522 may be inserted for the chamfer cuts, and so on. In addition, although slots are not shown, by placing the blade against the surfaces 530 (not visible) and 532, cuts corresponding to the sides of the box structure may be performed. Blades in positions 540 and 542 may be used to make the bottom cuts associated with the box. In the case of position 540, the blade could rest against a surface (not shown) provided on the device, whereas a slot 543 may be provided for a deeper box bottom cut using blade 542.

Figure 6:
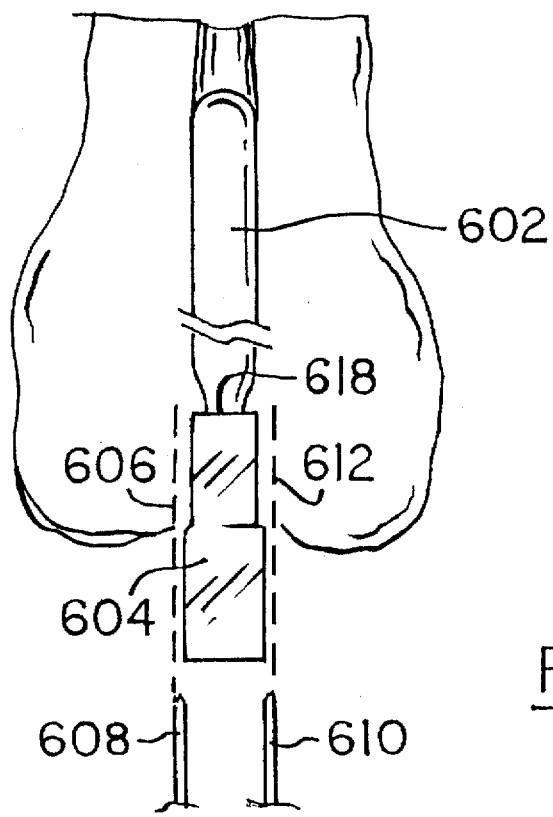
FIG. 6 is a top view of yet a further alternative embodiment of the invention involving the use of a box-cutting implement which may be removed from an implanted stem onto which a combination trial and cutting guide may subsequently be installed.
Figure 7:
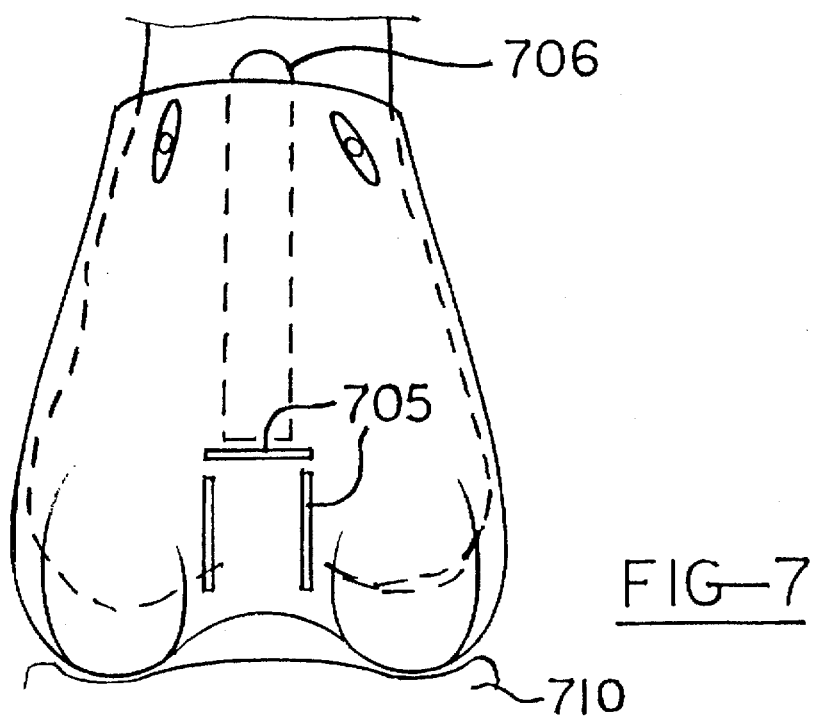
FIG. 7 is a top view drawing of the combination trial/cutting guide referenced above with regard to FIG. 6, now in position on the implanted stem.

FIGS. 6 and 7 illustrate a further alternative embodiment for accurately providing box cuts in the event that such cuts were not performed previously. In FIG. 6, there is shown a block 604 removably attached to an implanted intermedullar stem 602. Once in place, a saw blade at position 608 may be moved along the left surface of the block 604 to make a side box cut 606, and a blade in position 610 may be moved along a right surface of the block 604 to make a box cut 612. As an alternative to the use of outer surfaces of a cutting block such as 604, a guide with slots may also be removably attached to the stem 602. To make the bottom cut of the box, a blade may be moved straight down into the page, riding against a rearward surface 618.

Now making reference to FIG. 7, a device similar to that depicted in FIG. 5 is shown generally at 702. Instead of providing a passageway 506 against which a flat saw may be placed to provide the box cuts, separate slots 705 are provided specifically for this purpose. This particular device may include a stem 706, but since the box cuts are not yet available, a trial is carried out in conjunction with a specialized tibial spacer 710 not having superior post protrusions should the joint configuration be stabilized in this manner. Once the cuts 705 are performed, the overall device may be removed from the stem 706, and, assuming the stem connection is sufficiently deep in the bone, the cut corresponding to the bottom of the box may be completed. Then a device such as that shown in FIG. 4 may be inserted, as required, to carry out any necessary subsequent resections.

Figure 8:
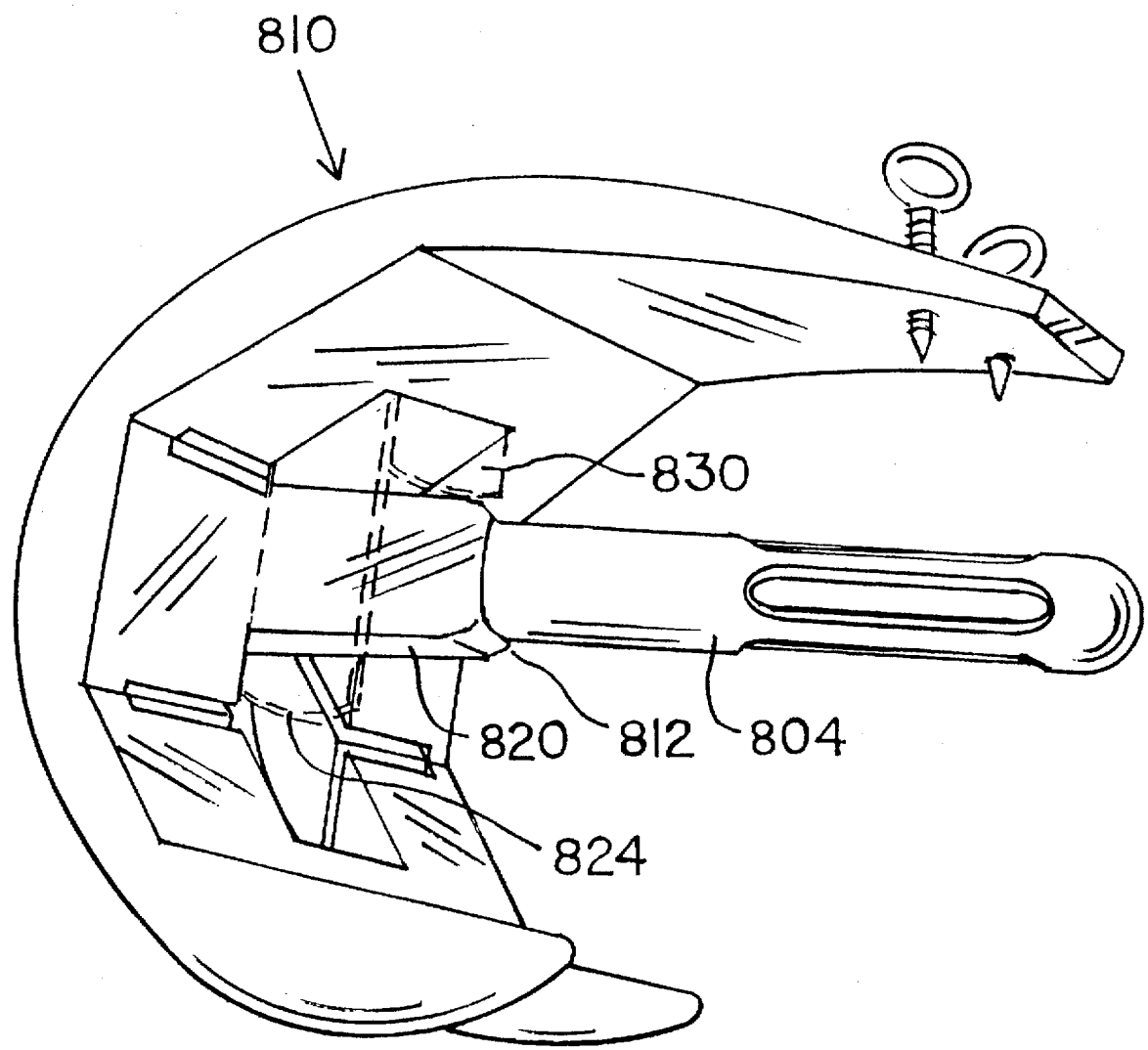
FIG. 8 is yet a further alternative embodiment of the invention including a stem configuration which facilitates at least partial box cut formation along with guides for other resections in a femoral knee application.

FIG. 8 shows yet another further alternative embodiment of the invention. In this particular design, a stem 804 is provided, which is removably attachable to the bulk of the trial/cutting guide assembly 810 at an interface 812. As a compromise between the passageway 506 shown in FIG. 5 and the complete box structure 404 shown in FIG. 4, the stem 804 connects to a smaller box-shaped element 820, enabling a saw to be placed on either side to perform the side box cuts, as shown in phantom at 824 for the one side, or used from above to form the bottom surface of the box with a saw shown at position 830. Having carried out at least this partial bottom surface cut, the bulk of the element may be removed from the stem 804 at interface 812 and the saw in position 830 extending downwardly to finish off the bottom box surface cut. With the box cuts having been performed and with the stem 804 remaining in place, a device such as that shown in FIG. 4, with the stem 450 being removable from the box 404 at the interface 460, may then be installed and the remaining resections performed.

In use, then, the invention affords a procedure which, in at least one respect, is essentially opposite to steps now being performed. That is, rather than making the various cuts (including the use of different saw guides), then performing a trial reduction, by using the present invention, in essence, a trial reduction is performed first with a trial having saw guide slots or surfaces. Once the various cuts have been made, the inventive combined trial/saw guide is removed, at which point the surgeon realizes precisely which final implant to choose for permanent affixation. Not only will the surgeon know which final prosthetic component to select, but he or she will also know which spacers to use based upon the depth of slot used for the cut, and, since the combined trial/saw guide of this invention may be constructed with prior knowledge of the final implant configuration, misalignments of the type discussed earlier with regard to the implant stem are minimized. Due to the fact that a single guide may be used to perform numerous, accurate cuts, the invention should save considerable time while increasing the precision of both primary and revision arthroplasty in a wide variety of joint replacement and other orthopaedic situations including the tibial side of a knee replacement.

Having thus described my invention, I claim:

1. The method of preparing an end of a bone having surfaces requiring resection in order to receive a joint-related implant, comprising the steps of:

providing a combination trial and cutting guide;

installing the combination trial and cutting guide onto the end of the bone before performing any of the resections;

reducing the bone with the guide installed to test the joint; and upon a satisfactory reduction, with the cutting guide installed, performing all of the resections, as required.

2. The method of claim 1, wherein the end of the bone is a distal femur, and wherein the step of providing a combination trial and cutting guide includes the step of providing such a guide having outer condylar surfaces configured to co-act in a knee joint.

3. The method of claim 2, wherein the combination trial and cutting guide includes bone-modification guides capable of performing a distal cut and a posterior cut.

4. The method of claim 2, including the step of providing a combination trial and cutting guide includes one or more guides capable of performing a box cut of the type associated with cruciate-sacrifice knee-replacement surgery.

5. In revision knee arthroplasty, wherein a final implant having outer condylar surfaces and an intercondylar box structure associated with a cruciate-sacrificing procedure is to be installed onto the distal end of a femur, the method of preparing the femur to receive the final implant, comprising the steps of:

performing a series of box cuts into the end of the femur sufficient to receive the box structure, including the steps of:
installing an intermedullary guide post,
installing onto the guide post, a rectangular structure having surfaces which correspond to the box cuts, and
performing the box cuts using the surfaces of the rectangular structure as references, providing a trial implant having outer condylar surfaces and a box structure which correspond to those of the final implant, the trial implant further including a plurality of bone-modification guides sufficient to perform all anterior, posterior, angled, and axial resections necessary to receive the final implant;

installing and securing the trial implant to the distal end of the femur;

performing a trial reduction with the trial implant in place; and in the event of a successful trial reduction, performing all required resections using the bone-modification guides, removing the trial implant, and installing the final implant.

6. A trial implant for femoral revision knee arthroplasty including a cutting guide for performing box cuts associated with a cruciate-sacrificing procedure, the trial comprising:

a solid body having an outer condylar surface and a plurality of inner surfaces which correspond to resected surfaces on the distal end of a femur; and a rectangular aperture formed through a central region of the body, the aperture having one or more side surfaces which may be used as references to perform the box cuts.

7. The trial of claim 6, further including one or more slots into which a saw blade may be inserted to trim one of the resected surfaces.

8. The trial of claim 6, wherein the spacing between the outer condylar surface and that of at least one of the inner surfaces is slightly less than the corresponding thickness of the final implant to account for the thickness of the saw blade.

* * * * *